United States Patent
Neumiller et al.

(10) Patent No.: US 8,179,087 B2
(45) Date of Patent: May 15, 2012

(54) SELECTIVE RECHARGING OF MEDICAL DEVICE DEPENDING ON AUTHENTICATION OF POWER ADAPTER SYSTEM

(75) Inventors: James S. Neumiller, Redmond, WA (US); John C. Daynes, Redmond, WA (US); Kenneth J. Peterson, Bellevue, WA (US); Thomas J. McGrath, Everett, WA (US); Richard C. Nova, Kirkland, WA (US)

(73) Assignee: Physio-Control, Inc., Redmond, WA (US)

( * ) Notice: Subject to any disclaimer, the term of this patent is extended or adjusted under 35 U.S.C. 154(b) by 293 days.

(21) Appl. No.: 12/760,378

(22) Filed: Apr. 14, 2010

(65) Prior Publication Data
US 2010/0198287 A1 Aug. 5, 2010

Related U.S. Application Data

(63) Continuation-in-part of application No. 12/131,267, filed on Jun. 2, 2008, now Pat. No. 7,728,548.

(51) Int. Cl.
*H02J 7/00* (2006.01)
*A61N 1/39* (2006.01)
(52) U.S. Cl. ............... 320/106; 607/5; 607/29; 607/60; 607/61; 320/166
(58) Field of Classification Search .................. 320/106; 607/5, 29, 60, 61
See application file for complete search history.

(56) References Cited

U.S. PATENT DOCUMENTS

| | | | |
|---|---|---|---|
| 5,321,392 A | 6/1994 | Skakoon et al. | |
| 5,702,431 A * | 12/1997 | Wang et al. ............... | 607/61 |
| 5,721,482 A | 2/1998 | Benvegar et al. | |
| 5,939,856 A | 8/1999 | Demuro et al. | |
| 6,072,299 A | 6/2000 | Kurle et al. | |
| 6,127,063 A | 10/2000 | Kowalsky et al. | |
| 6,181,102 B1 | 1/2001 | Andrews et al. | |
| 6,223,077 B1 | 4/2001 | Schweizer et al. | |
| 6,249,105 B1 | 6/2001 | Andrews et al. | |
| 6,291,966 B1 | 9/2001 | Wendelrup et al. | |
| 6,438,415 B1 | 8/2002 | Powers | |
| 6,639,381 B2 | 10/2003 | Tamura et al. | |
| 6,873,133 B1 | 3/2005 | Kavounas | |
| 6,972,542 B2 | 12/2005 | Patino et al. | |

(Continued)

FOREIGN PATENT DOCUMENTS

KR 20040095307 A 11/2004

OTHER PUBLICATIONS

International Preliminary Report on Patentability for PCT/US20091045943, dated Sep. 1, 2010 (12 pp.).

(Continued)

*Primary Examiner* — M'Baye Diao
(74) *Attorney, Agent, or Firm* — Marger Johnson & McCollom PC

(57) ABSTRACT

In an embodiment, a medical device can be used with a power adapter system. In addition, it can receive a data set from the power adapter system, and examine the data set to determine whether the data set confirms or not an authentication of the power adapter for use with the medical device. If the authentication is not confirmed, the external medical device can operate differently than otherwise. For example, power can be drawn more slowly from the power adapter system.

18 Claims, 4 Drawing Sheets

U.S. PATENT DOCUMENTS

| | | |
|---|---|---|
| 7,095,210 B2 | 8/2006 | Tamura et al. |
| 7,250,612 B2 | 7/2007 | Pai-Paranjape et al. |
| 7,728,548 B2 | 6/2010 | Daynes et al. |
| 2003/0195581 A1* | 10/2003 | Meadows et al. ............... 607/29 |
| 2006/0178170 A1 | 8/2006 | Chung et al. |
| 2007/0143864 A1 | 6/2007 | Cabana et al. |
| 2008/0140163 A1* | 6/2008 | Keacher et al. ................ 607/60 |

OTHER PUBLICATIONS

U.S. Appl. No. 121760,331, James S. Neumiller, filed Apr. 14, 2010.
International Search Report and Written Opinion of international application No. PCT/US20091045943, mailed May 4, 2010, 14 pp.
Response to Written Opinion for PCT/US2009/045943 filed Aug. 2, 2010. (18 pp.).

* cited by examiner

SELECTIVE RECHARGING OF MEDICAL DEVICE DEPENDING ON AUTHENTICATION OF POWER ADAPTER SYSTEM

CROSS REFERENCE TO RELATED PATENT APPLICATIONS

This patent application is a continuation-in-part of co-pending U.S. patent application Ser. No. 12/131,267, filed on Jun. 2, 2008, by the same inventors, entitled DEFIBRILLATOR BATTERY AUTHENTICATION SYSTEM, all commonly assigned herewith, the entire content of which is incorporated herein by reference.

This patent application may be found to be related to U.S. patent application Ser. No. 12/760,331, filed on the same day as the instant patent application, by the same inventors, entitled SELECTIVE POWERING OF MEDICAL DEVICE DEPENDING ON AUTHENTICATION OF POWER ADAPTER SYSTEM, all commonly assigned herewith, the entire content of which is incorporated herein by reference.

FIELD

This invention generally relates to external defibrillators. More particularly, the invention relates to how an external defibrillator might authenticate its power adapter.

BACKGROUND

Defibrillators are medical devices for providing life-saving electrical therapy to persons experiencing an irregular heart beat, such as ventricular fibrillation (VF). A defibrillator provides an electrical stimulus to the heart in an attempt to convert the irregular heart beat to a normal sinus rhythm. An external defibrillator sends electrical pulses to the patient's heart through external electrodes applied to the patient's chest.

The typical external defibrillator is capable of being powered by external power, via a power adapter. The power adapter may power the defibrillator directly, or recharge a rechargeable battery of the defibrillator. Because defibrillators are intended for use in life-threatening medical emergencies, their power adapter must meet high standards of safety and reliability. A defibrillator designed for use by ambulance crews and in hospitals typically will use power adapters designed specifically for that particular make and model of defibrillator.

Typical external defibrillators have a useful life longer than that of their power adapters. This necessitates the purchase and deployment of several replacement power adapters over the useful life of a single defibrillator. An external defibrillator owner may find several sources from which to purchase after-market power adapters which are configured to operate with the defibrillator, at least nominally. However, if an after-market power adapter is not manufactured to the appropriate quality standards, the performance of the defibrillator may suffer and safety may be compromised. Unfortunately, whether a particular power adapter meets standards and specifications set by the defibrillator manufacturer may not be readily apparent simply by examining the outward appearance of the power adapter.

BRIEF SUMMARY

The present description gives instances of devices, systems and methods, the use of which may help overcome problems and limitations of the prior art.

In an embodiment, a medical device can be used with a power adapter system. In addition, it can receive a data set from the power adapter system, and examine the data set to determine whether the data set confirms or not an authentication of the power adapter for use with the medical device. If the authentication is not confirmed, the external medical device can operate differently than otherwise. For example, power can be drawn more slowly from the power adapter system.

These and other features and advantages of this description will become more readily apparent from the following Detailed Description, which proceeds with reference to the drawings, in which:

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Aspects of the invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, look-up tables, or the like, which may carry out a variety of functions under the control of one or more processors or other control devices. In addition, those skilled in the art will appreciate that the present invention may be practiced in conjunction with any number of medical devices including practical defibrillator systems and that the system described herein is merely one example application. The connecting lines shown in the various figures contained herein are intended to represent example functional relationships and/or physical couplings between the various elements. It should be noted that many alternative or additional functional relationships or physical connections may be present in a practical embodiment.

Figure 1:
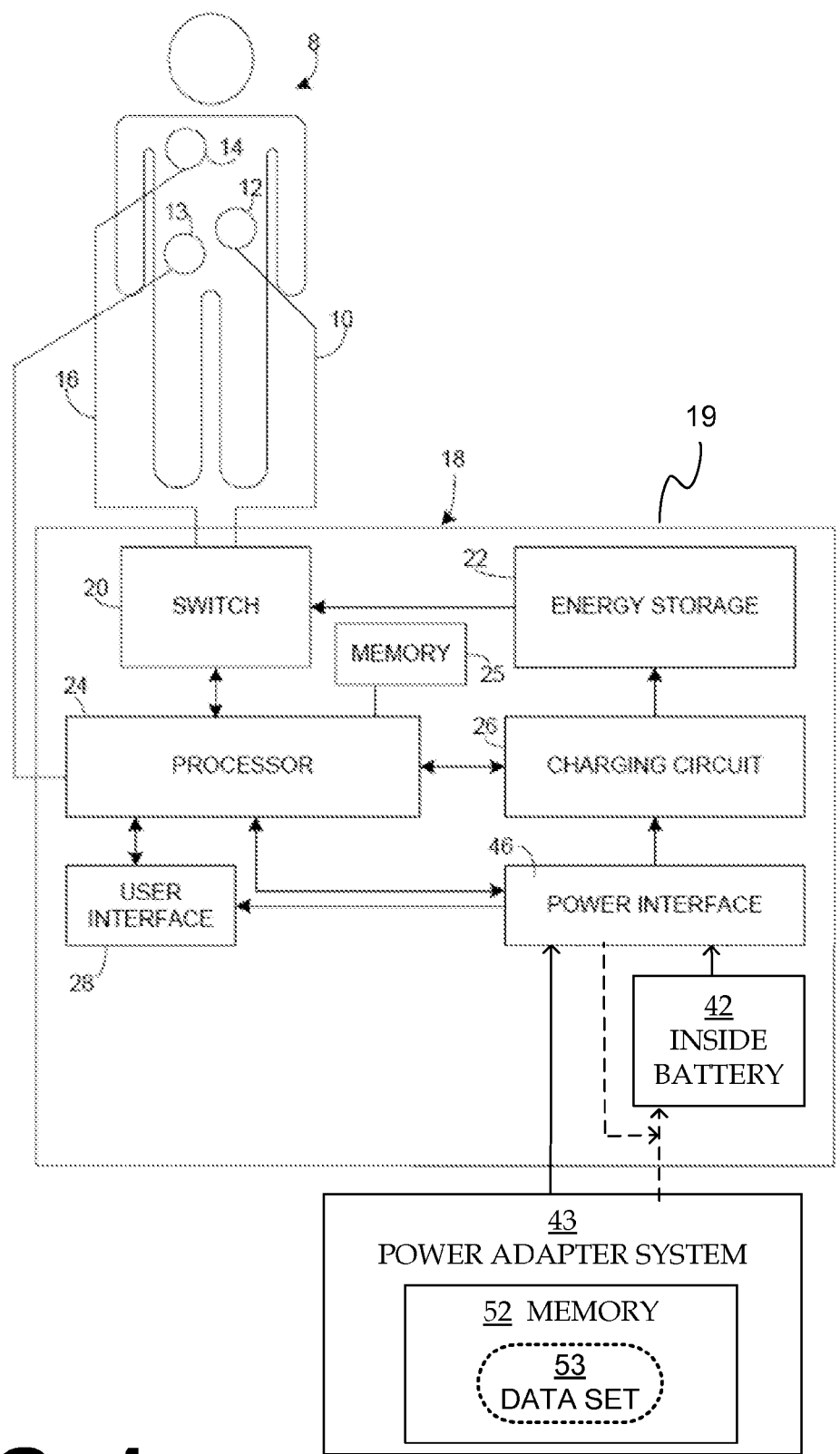
FIG. 1 is a schematic representation of an external defibrillator system configured to receive power via a power adapter system in accordance with embodiments.

FIG. 1 is a block diagram showing a patient 8 coupled to an external defibrillator 18 that is provided in a housing 19. Defibrillator 18 administers defibrillation therapy to patient 8 via electrodes 12 and 14. The body of patient 8 provides an electrical path between electrodes 12 and 14. Electrodes 12 and 14 are coupled to switch 20 via conductors 10 and 16. Switch 20 couples electrodes 12 and 14 to the output of an energy storage device 22. Switch 20 is of conventional design and may comprise an arrangement of solid-state devices such as silicon-controlled rectifiers or insulated gate bipolar transistors. These may be arranged in an H-bridge configuration.

Energy storage device 22 includes components such one or more capacitors that store the energy to be delivered to patient 8 via electrodes 12, 14. Before a defibrillation pulse may be delivered to patient 8, energy storage device 22 must be charged. A processor 24 analyzes the patient's ECG signals that are transmitted from electrodes 12, 14 (or, in some embodiments from separate sensing electrodes, not shown).

The processor 24 may be any general purpose processor, microprocessor, controller, or microcontroller that is suitably configured to control the operation of defibrillator. The processor 24 has a memory 25 associated with it. Memory 25 may be any suitable processor-readable medium, including an electronic circuit, a semiconductor memory device, a ROM, a flash memory, or the like. As described in more detail below, memory 25 is capable of storing patient data captured during a resuscitation event, as well as data which can be programmed into the memory 25 during defibrillator manufacturing or during the programming of software updates or upgrades by well-known means.

When the energy stored in energy storage device 22 reaches the desired level, defibrillator 18 is ready to deliver the defibrillation shock. Processor 24 may activate an element of a user interface 28 such as an indicator light, a visual display, or a speaker, that informs the operator that defibrillator 18 is ready to deliver a defibrillation shock to patient 8 or instructs the operator to push a shock button to activate switch 20 and thereby deliver a defibrillation shock to patient 8.

In a defibrillator 18 operating in an AED mode, the processor determines whether a defibrillating shock is advisable based on the ECG analysis and, if it is, directs a charging circuit 26 to charge energy storage device 22 to a high voltage level. Charging circuit 26 includes, for example, a flyback charger that transfers energy from a power source 30 to energy storage device 22.

Contrary to how a defibrillator operates in an AED mode, in a fully automatic external defibrillator, processor 24 causes the user interface 28 to prompt the operator that defibrillator 18 is ready to deliver a defibrillation shock to patient 8 and to refrain from touching the patient. Processor 24 then activates switch 20 to electrically connect energy storage device 22 to electrodes 12 and 14, and thereby deliver a defibrillation shock to patient 8.

An external defibrillator for use in a hospital or by emergency medical service providers (EMS), commonly called a defibrillator/monitor, may have patient parameter monitoring functionality. Such a defibrillator 18 may include patient parameter sensors 13 such as capnography, pulse oximetry, NIBP, EtCO2, invasive blood pressure, temperature, and other vital sign sensors. Its monitoring functionality may also include patient impedance and ECG (including 12-lead ECG) monitoring. Processor 24 may be configured to analyze sensor data to determine patient condition and to evaluate the efficacy of delivered therapy.

Sensor data and results of analyses may be stored in the defibrillator memory 25. The defibrillator 18 may also include sensors for monitoring CPR performance (for example, as a part of a CPR feedback or coaching system). These sensors may include accelerometers, force sensors, impedance sensors or other sensors that detect parameters from which chest compression depth, rate, force, or other characteristics of chest compressions may be determined.

The defibrillator 18 may also have cardiac pacing functionality and synchronized cardioversion functionality in addition to its defibrillation therapy functionality. Processor 24 also controls these therapy functions.

A defibrillator 18 such as a defibrillator/monitor may have the capability to function in a manual mode, in which the user chooses one or more parameters of defibrillation therapy delivery such as energy level dosage and timing of delivery, and also in the AED mode described above, where the processor 24 controls therapy delivery parameters. The user interface 28 may include an element which receives an indication of whether the user has chosen manual mode or AED mode, with this choice being communicated to the processor 24. The processor 24 then controls the defibrillator functionality accordingly.

Processor 24 may perform other functions as well, such as controlling the user interface delivery of information concerning the status and operation of the defibrillator and battery pack(s) or other power source engaged with the defibrillator. The user interface may include a screen or other visual display that can display text messages, graphics or pictures that communicate the authenticity of the power adapter system. The user interface may include an audio interface such as a speaker through which voice prompts or other audio signals.

Defibrillator 18 may be made with various sources of power. In the embodiments of FIG. 1, defibrillator 18 includes an inside battery 42. While a single inside battery 42 is shown, more could be included. By "inside battery", it is meant any device that stores electrical energy electrochemically or through any other storage mechanism such as solar cells, flywheels, for example. An inside battery may include, for example, an arrangement of one or more conventional electrochemical cells or fuel cells.

Inside battery 42 is preferably a smart battery capable of self-monitoring and communicating its charge level, maintenance needs and conditions that indicate replacement is needed. An example of a smart battery suitable for use in the defibrillator 18 is discussed in detail in U.S. Pat. No. 6,072, 299, which is hereby incorporated by reference herein in its entirety. It is advantageous but not necessary that inside battery 42 be rechargeable.

Inside battery 42 could be removable from housing 19, as a battery pack. It could be received in a battery well (not shown), or a compartment, or a slot, or other battery pack engaging mechanism of defibrillator housing 19. An example of a battery well interface suitable for use in the illustrated embodiment is discussed in detail in U.S. Pat. No. 6,127,063 which is hereby incorporated by reference herein in its entirety.

Alternately, inside battery 42 could be fixed within housing 19, and internal to the defibrillator 18. In such embodiments, inside battery 42 may be charged by a method which does not require direct physical contact with a charging device. For example, inside battery 42 may be charged via a wireless charging method such as inductive charging while the defibrillator is engaged with a docking station.

The defibrillator 18 is intended to also receive power via a power adapter system 43, made according to embodiments. Examples are now described.

Figure 2:
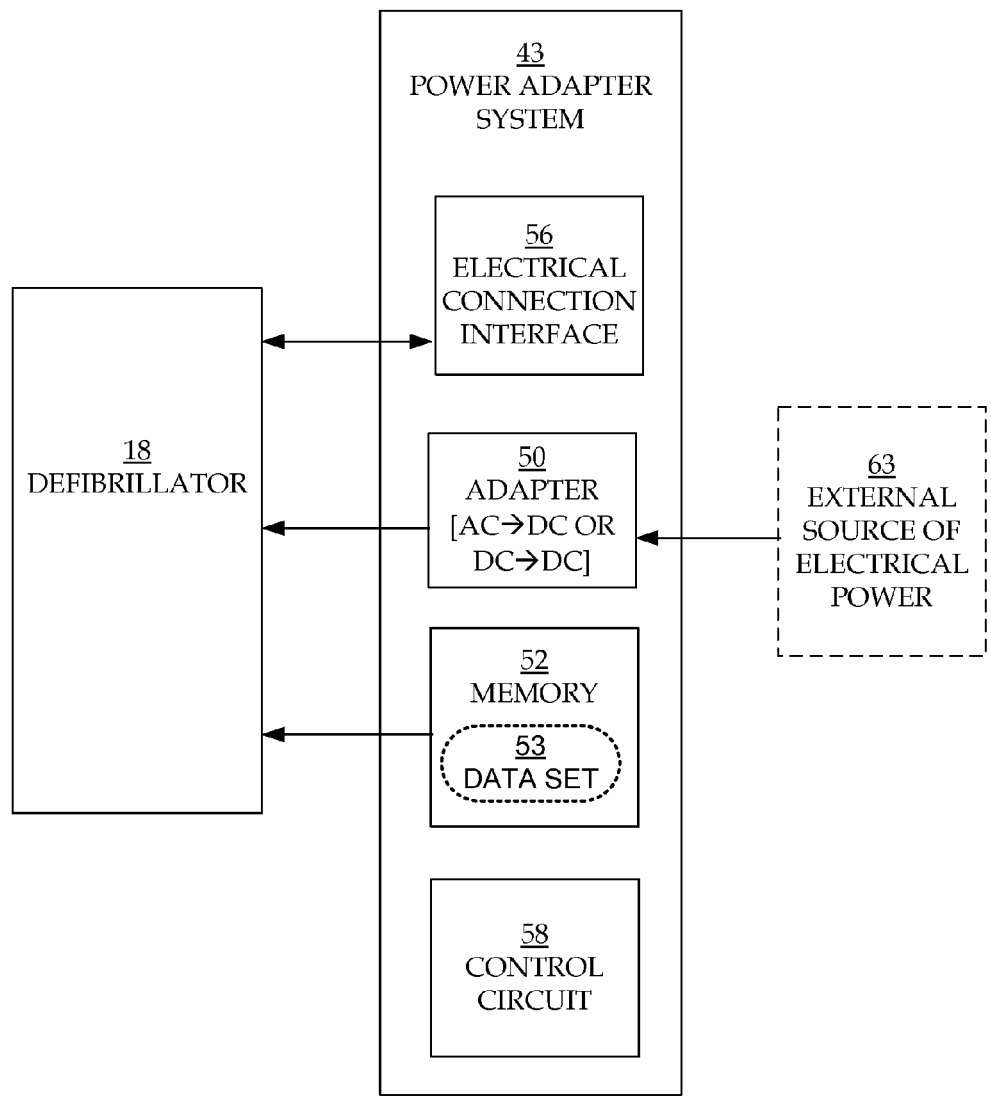
FIG. 2 is a block diagram for a power adapter system that can be used to power the defibrillator of FIG. 1.

Referring now also to FIG. 2, power adapter system 43 includes an adapter 50 for adapting electrical power available from an external source 63. The adapter 50 is a converter, and is constructed according to how power is received from the intended source 63, which can be AC or DC. For example, the adapter 50 could be an AC/DC adapter, which can convert AC electrical power from a wall outlet. Or, the adapter 50 could be a DC/DC adapter, which can convert DC electrical power from the battery of a vehicle, such as an ambulance or a fire truck. Or, the adapter 50 could be an AC/DC adapter, which can convert AC electrical power from the ambulance or a fire truck.

Power adapter system 43 can be electrically coupled with defibrillator 18. This electrical coupling can be performed in a number of ways. In some embodiments, suitable power cables can be used. In some embodiments, power adapter system 43 can be physically attached to housing 19, although that is not necessary for practicing the invention. Such physical attachment can be accommodated by a implementing a suitable receiving structure in housing 19. An example of such a structure is a well, for partial or complete insertion of power adapter system 43 therein.

Returning to FIG. 1, when power adapter system 43 is electrically coupled with defibrillator 18, it further becomes electrically coupled to a power interface 46 in the defibrillator 18. Power interface 46 delivers power from either inside battery 42, or power adapter system 43 to the processor 24, charging circuit 26 and user interface 28. The power interface 46 includes circuitry which can automatically switch from one power source to the other, depending on factors. Such factors can be, for example, the relative charge levels of the two sources. An example of a power delivery interface and battery switching circuit suitable for use in the illustrated embodiment is discussed in detail in U.S. Pat. No. 6,223,077, which is hereby incorporated by reference in its entirety. Other examples are described later in this document.

Returning to FIG. 2, power adapter system 43 additionally includes a memory 52. Memory 52 has stored therein a data set 53 that can be used to authenticate power adapter system 43 as is described in more detail below.

Power adapter system 43 can further optionally include a control circuit 58. Control circuit 58 can assist in the reading of data set 53, by enabling the memory, assisting with encryption, etc. In some embodiments, control circuit 58 in FIG. 2 can assist in the reading of a memory, if provided, of inside battery 42, thereby determining the authenticity of battery 42 as already described in co-pending U.S. patent application Ser. No. 12/131,267, filed on Jun. 2, 2008, entitled DEFIBRILLATOR BATTERY AUTHENTICATION SYSTEM. If battery 42 is an authentic part intended for use with defibrillator 18 then full functionality of power adapter 43 as related to recharging battery 42 will be allowed. If battery 42 is not authentic, system functionality may be limited as described above.

Power adapter system 43 may also include an electrical connection interface 56. Electrical connection interface 56 may include one or more electrical connectors that mate with corresponding electrical connectors in housing 19 to form an electrical path between the adapter 50 and the power interface 46 to transmit power from power adapter system 43 into the defibrillator 18. Moreover, the whole power adapter system 43 may be provided with or without additional cables, which can terminate in connectors, etc. Electrical connection interface 56 can be made in a number of ways, for data set 53 to be received by defibrillator 18. Two examples are now described.

Figure 3:
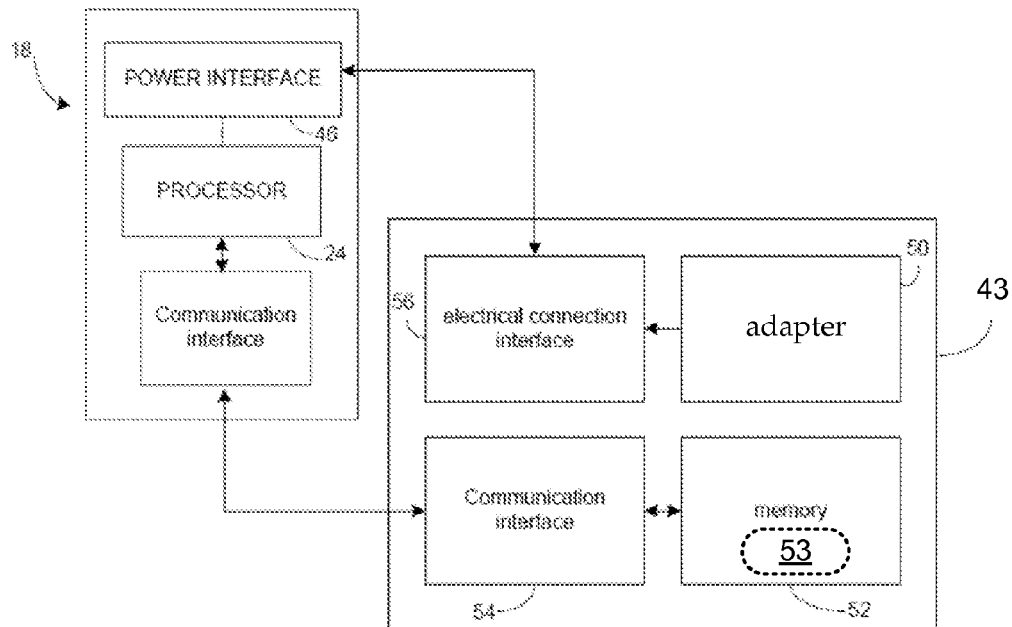
FIG. 3 is a schematic representation of a first example of a power adapter system for use in the defibrillator of FIG. 1.

Referring to FIG. 3, power adapter system 43 of FIG. 3 also includes a communication interface 54 which communicates data from memory 52 into the defibrillator 18. The communication interface 54 in FIG. 3 may be a wireless communication interface 54 which communicates with a wireless communication interface in the defibrillator 18. For example, well-known wireless communication techniques in accordance with a standardized data communication protocol such as Bluetooth; IEEE 802.11 (any variation thereof); Ethernet; IEEE 1394 (Firewire); GPRS; USB; IEEE 802.15.4 (ZigBee); IrDA (infrared) or induction, may be used to form a communication link between the power adapter system 43 and the defibrillator 18. Or it could be signal wires for transferring signals, above and beyond the power wires for transferring the power.

Figure 4:
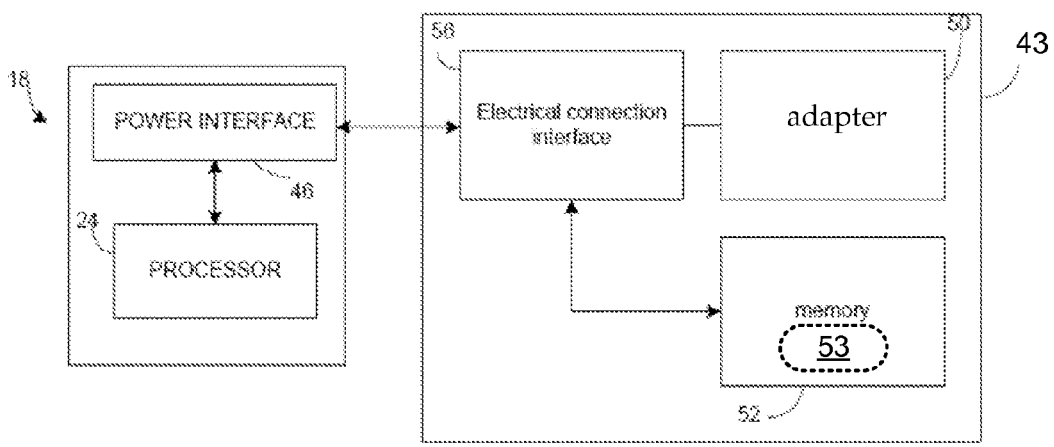
FIG. 4 is a schematic representation of a second example of a power adapter system for use in the defibrillator of FIG. 1.

FIG. 4 shows a different embodiment of power adapter system 43. A communication interface, not shown as a separate component, may be a hard-wired communication interface which forms part of the electrical connection interface 56. In this case, it will communicate data set 53 using well-known techniques such as that described in U.S. Pat. No. 6,127,063, which has been discussed above. In some embodiments, data set 53 can be encoded as a modulated signal onto the power signal that is delivered to the defibrillator from adapter 50.

Returning to FIG. 1, data set 53 can be programmed into the memory 52, preferably during the manufacturing process. The authenticating party may be the defibrillator manufacturer or a party that the defibrillator manufacturer has authorized and directed to program authentication information into the memory 52 (for example, an authorized after-market manufacturer). The data set 53 as such encodes authentication information. The data set 53 is recognizable by the processor 24 in the defibrillator as a data set that confirms authentication. The data set may be encrypted. It may include a digital key which the defibrillator processor 24 must recognize in order to authenticate the power adapter system 43. As additional security measures to safeguard against counterfeiting, the digital key or other authenticating data programmed into memory 52 may be varied by the authorizing party with corresponding variations in authentication data recognition software that are programmed into defibrillators at various times, for example, during periodic defibrillator software upgrades. For example, authenticating data can be varied according to year of manufacture, or according to a schedule that corresponds to a defibrillator manufacturer's distribution of software updates for its defibrillators.

The data set can be received spontaneously, or upon querying, etc. More particularly, in some embodiments, the processor 24 is configured to cause the defibrillator 18 to query a power adapter system that has been coupled with it, for its authenticating data set. This query may be transmitted to the power adapter system via the power interface 46. An authorized power adapter system will respond by transmitting the authentication data set. Alternatively, the power adapter system may be configured to send its authenticating data set to the defibrillator upon its coupling with the defibrillator, or upon powering on of the defibrillator, with no query from the defibrillator being needed. A processor may be configured to query its power adapter system when the defibrillator performs a self-test procedure. In embodiments using a wireless communication link between the power adapter system and the defibrillator, the query may be given before the power adapter system becomes coupled with housing 19. For example, a query may be given when the power adapter system is brought into proximity of the defibrillator. In another embodiment, an actuator or interface control may be provided, such as a status button, which provides status information on the power adapter system when actuated.

In some embodiments, defibrillator 18 also includes a display (not shown), such as a screen. The display can be controlled to display at least a portion of the data set learned by the power adapter system. For example, it can show the manufacture date, usage data, etc.

In some embodiments, if no data set is received from power adapter system 43, then the authentication is not confirmed. For example, an unauthorized power adapter system might not even have a memory such as memory 52.

If data is transmitted from a power adapter system to the processor 24, the processor 24 will analyze the data to determine if it is an authenticating data set. This may be done in any of several ways. For example, the defibrillator processor may verify that the data set includes the authorized digital key. Or, the processor may compare the transmitted data set to one or more data sets stored in defibrillator memory 25 to see if the transmitted data set matches one stored in the defibrillator memory.

It may be advantageous for an authorizing party to program more than one set of identifying data into each defibrillator, so that one of several different corresponding authentication data sets may be used in an authorized power adapter system. This may be advantageous for allowing pre-planned changes in programmed authorization data sets (for example, data set A programmed into power adapter systems in manufacturing year X; data set B in manufacturing year Y, etc.), or if several different manufacturers will be authorized, to provide a different authorization data set for each one.

The identifying data set 53 may be programmed into the defibrillator at the time of defibrillator manufacture. Programming of identifying data may be updated from time to time. Software in a defibrillator is sometimes modified or replaced in order to upgrade or update performance of the defibrillator. A modification or replacement of previously programmed identifying data may be made as a part of a software upgrade, or the reprogramming of identifying data may be made independently of any other defibrillator software upgrade.

In a number of embodiments, defibrillator 18 can operate differently depending on whether or not the preset authentication about the power adapter system is confirmed. In other words, if the authentication is confirmed, defibrillator 18 can operate according to a first protocol, which is also known as the authenticated protocol. But if the authentication is not confirmed, defibrillator 18 can operate according to a second protocol, which is also known as the non-authenticated protocol. A number of protocols can be designed accordingly, as will be apparent from the examples in this document.

In a number of embodiments, the second protocol represents a more limited functionality level than the first protocol. So, the two protocols can be represented as two levels of functionality.

A non-authorized protocol may include one or more of: a reduced or modified functionality of the defibrillator, a modification of information provided to the user concerning the power adapter system.

Moreover, the user can be notified of whether the authentication about power adapter system is confirmed or not. Notification could be by using the interface of defibrillator 18.

The non-authenticated protocol may include the step of notifying a user of the non-authorized status of the power adapter system. A recommendation can be displayed for replacing the unauthenticated power adapter, or a warning can be displayed against its use. Plus, limiting the functionality of the defibrillator can be by limiting or disabling an information display or an information storage function. For example, question marks can be displayed. Moreover, the notification can show which functionality is not available, because the authentication is not confirmed.

In one example, according to the first protocol, power is drawn from the power adapter system 43 even if inside battery 42 is charged, but according to the second protocol, power is drawn from the power adapter system 43 only if the inside battery is not charged. In other words, the non-authenticated protocol may include drawing power from the non-authenticated power adapter system only if it is the only available source of power for the external medical device. This may further include the steps of: before drawing power from the non-authenticated adapter, determining whether an alternative power source is coupled to the medical device, and determining whether power is available from that alternative power source.

In another example, the inside battery 42 is rechargeable. According to the first protocol, power can be drawn from the power adapter system to recharge the inside battery at a first charging rate. The first charging rate is preferably the full charging rate. According to the second protocol, however, power can be drawn from the power adapter system to recharge the inside battery at a second charging rate, which is less than the first charging rate. The second charging rate can be a fraction of the first charging rate, even zero. This can be accomplished by a number of ways, as will be determined by a person skilled in the art, for example shunting, etc. In other words, the power adapter system may charge more slowly, if at all. In some instances this feature is fixed. In others the second charging rate can be increased if an input is received from a user. Such an input would be an acknowledgement to a notification that the authentication failed, and to tend to it. Moreover, the number of charge cycles which a defibrillator will perform on any non-authenticated power adapter system can be limited in number. The time duration for use of an unauthenticated power adapter could be limited to a time chosen to accommodate a typical patient usage of the defibrillator, for example, 20 minutes, to avoid an interruption of therapy and monitoring.

The external medical device may be a defibrillator which has the capability of operating in both of a manual mode and an AED mode, and the step of limiting the functionality of the defibrillator may include limiting the functionality to AED mode.

The step of limiting the functionality of the defibrillator may include limiting the patient parameter monitoring functionality of the defibrillator. The step of limiting the patient parameter monitoring functionality of the defibrillator may include the step of disabling one or more of capnography, pulse oximetry, non-invasive blood pressure (NIBP) monitoring, end-tidal CO2 (EtCO2) monitoring, electrocardiogram (ECG) monitoring (which may include 12-lead ECG monitoring), invasive blood pressure monitoring, temperature monitoring, or monitoring of CPR performance (for example, as in a CPR feedback or coaching system).

In an embodiment where the medical device is a defibrillator, the step of limiting the functionality of the defibrillator may include disabling or limiting pacing therapy. The step of limiting the functionality of the defibrillator may include disabling synchronized cardioversion therapy. The step of limiting the functionality of the external medical device may include disabling a charging function of energy storage 22.

The step of limiting functionality of the defibrillator may include the step of disabling a post-processing function performed on one or more monitored parameters such as those mentioned above. For example, acute myocardial infarction (AMI) detection or alarms, or determination of heart rate or respiration rate, and/or alarms based on a heart rate or respiration rate could be disabled or limited.

The step of limiting functionality of the defibrillator may include the step of limiting or disabling an information storage, transfer or display functionality of the defibrillator. This may include disabling a printer built into the defibrillator, or limiting data transfer out of the defibrillator to a separate printer. Other examples include limiting the information displayed on a user interface display screen and/or limiting the information stored in the defibrillator's memory. For example, a defibrillator may be configured to display only ECG waveforms and no others, to display only a limited set of patient parameters and omit display of others, or to display detected parameters on the defibrillator display screen but not in a printed report. Other alternatives include storing a limited set of patient parameter data (i.e., limited to only certain parameters) or limit the storage time of patent parameter data.

In another alternative, the presence of an unauthorized power adapter with the defibrillator can be recorded in a code summary, in which information concerning usage of the defibrillator is recorded for post event review. It can alternatively or additionally be recorded in the defibrillator's device status log or self-test activity log so that personnel who review the device's status information and self-test results are aware that an unauthenticated power adapter had been in the device, and its warranty is possibly not covered.

In embodiments where the defibrillator has the capability to communicate with a remote unit (for example, a remote device management system) the defibrillator can communicate the confirmation or not of the authentication to the remote unit. If the defibrillator is adapted for two-way communication, the remote unit may, upon receiving a notification of lack of authentication confirmation, send to the defibrillator a communication including an instruction for the processor to cause a particular action to occur. This may be an instruction to shut down the defibrillator or to modify the processes performed by the defibrillator in some way. The instruction may be provided according to an algorithm performed by a processor at the remote unit (for example, to perform according to one or more of the protocols discussed elsewhere). Alternatively, the instruction to be sent back to the defibrillator may be determined by personnel monitoring authentication information at the remote unit.

While two levels of functionality have been discussed in connection with the illustrated embodiment, a system could have several functionality levels or several adapter use protocols which are invoked based on several authentication status levels. A functionality level or protocol may be chosen based on authentication status level, or upon other information transmitted from the battery pack to the defibrillator. For example, authenticated power adapter systems from certain manufacturers, manufacturing facilities, manufacturing lots or dates of manufacture, may be given a first authentication status (e.g., "level 1"), while those of others may be given a second authentication status (e.g., "level 2"), which correspond to a first and a second functionality level or protocol. For example, a first authentication level may correspond to a protocol or functionality level that include features (such as a visual message) which draw a user's attention to battery pack status, while a second authentication level may include modifications to defibrillator functionality which would encourage prompt power adapter replacement (such as a repeated audible prompt). The particular protocol or functionality level may be chosen based on the manufacturer/manufacturing facility, lot identification, manufacturing date or other factors.

This may be useful, for example, to draw a user's attention to a power adapter system that is nearing its expiration date by providing a protocol that includes prompts or displays that draw attention to this, and which may include defibrillator functionality modifications that encourage prompt power adapter system replacement. As another example, where a defibrillator manufacturer has become aware of an issue in a particular manufacturing lot or in power adapter system manufactured at a particular facility or in a particular data range which makes their replacement desirable or necessary, defibrillators already in the field may be reprogrammed so that the reprogrammed defibrillators will recognize power adapter system which transmit information indicative of being in the affected lot, or form the particular facility or date range, as being non-authenticated or as having an authentication status at a level which results in a modified protocol or functionality level as discussed above.

Figure 5:
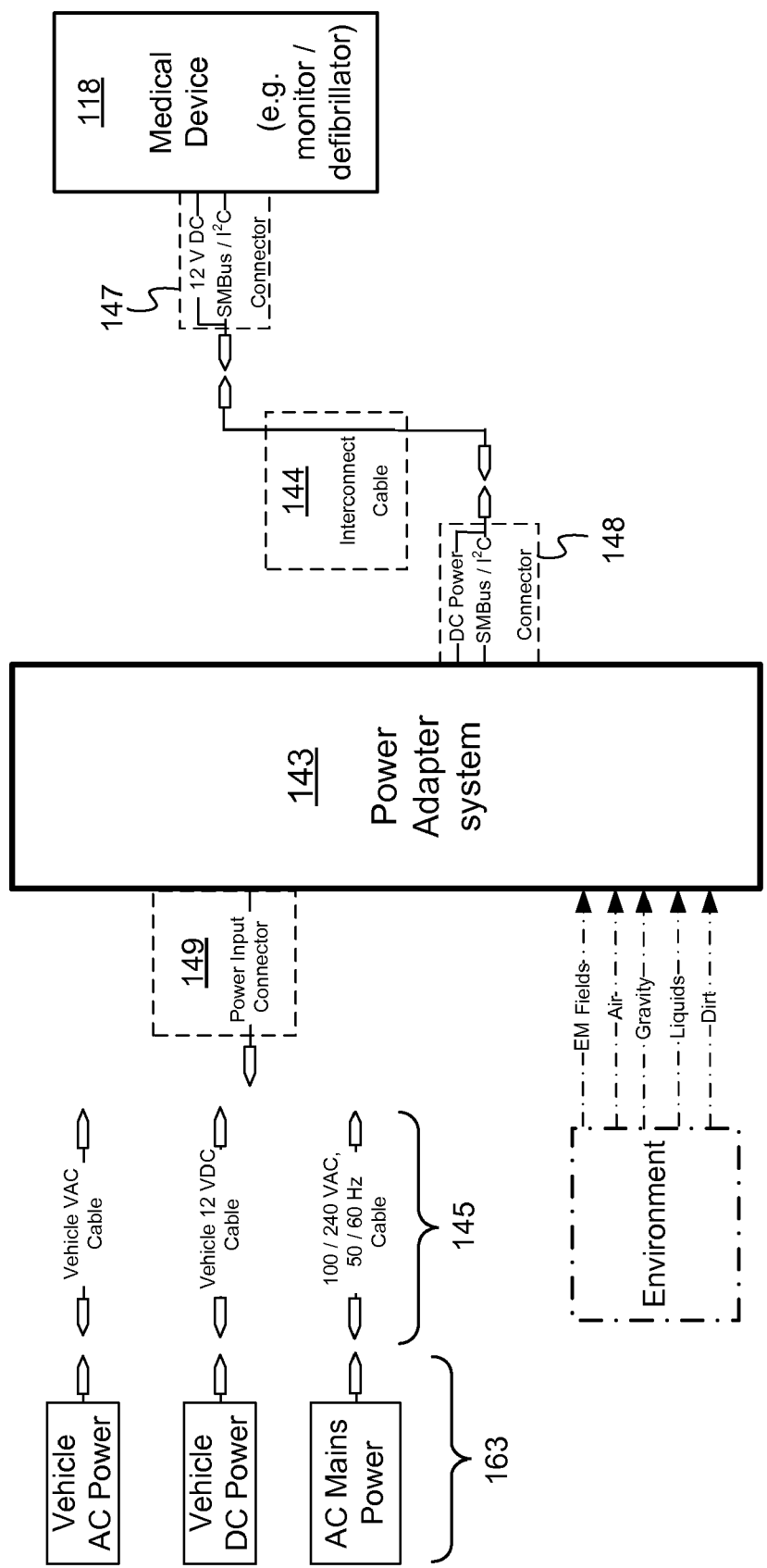
FIG. 5 is a schematic representation of components of the arrangement of FIGS. 1 and 2 according to embodiments.

FIG. 5 is a schematic representation of components of the arrangement of FIGS. 1 and 2 according to embodiments. A power adapter system 143 is constructed as has been described above in connection with power adapter system 43. In addition, it could have additional adapters internally, more than the single adapter 50, to accommodate different external power sources.

Power adapter system 143 is intended to adapt power from any one of external power sources 163 as shown. For each case, an appropriate one of alternate cables 145 can be used, to connect to a power input connector 149 of power adapter system 143.

Power adapter system 143 is intended for use with medical device 118 that can be constructed as has been described above in connection with defibrillator 18. Power adapter system 143 can be electrically coupled with medical device 118 via an interconnect cable 144. Interconnect cable 144 passes both the adapted power, and also includes a standard data communication interface like I2C or SMBus. This interface provides for communication over signal lines separate from the power lines.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. A medical device that is to receive power via a power adapter system, the medical device capable of operating to defibrillate a patient according to a first protocol if a preset authentication about the power adapter system is confirmed, and capable of operating to defibrillate the patient according to a second protocol different from the first protocol if the authentication is not confirmed, the medical device comprising:
    a housing;
    a capacitor for storing an electrical charge that is to be delivered to the patient as part of defibrillating according to either the first protocol or the second protocol;
    a rechargeable inside battery in the housing distinct from the power adapter system and capable of storing an electrical charge that is to be delivered to the capacitor, the rechargeable inside battery having a full charging capacity;
    means for receiving a data set from the power adapter system when the power adapter system is coupled with the housing; and a processor capable of recognizing whether the received data set confirms the authentication or not, in which according to the first protocol, power can be drawn from the power adapter system to recharge the inside battery at a first charging rate, but according to the second protocol, power can be drawn from the power adapter system to recharge the inside battery at a second charging rate less than the first charging rate.

2. The medical device of claim 1, in which
the second charging rate is substantially zero.

3. The medical device of claim 1, in which
the second charging rate is increased if an input is received from a user.

4. The medical device of claim 1, further comprising:
a display for displaying at least a portion of the data set.

5. The medical device of claim 1, in which
if no data set is received from the power adapter system, the authentication is not confirmed.

6. The medical device of claim 1, in which
a query is transmitted to the power adapter system, and
the data set is received responsive to the query.

7. The medical device of claim 1, in which
the data set is received responsive to power-on of the device.

8. The medical device of claim 1, in which
the data set is received responsive to electrical engagement of the power adapter system with the housing.

9. The medical device of claim 1, in which
the received data set is encrypted.

10. The medical device of claim 1, in which
according to the first protocol, a first type of indication about a status of the power adapter system is displayed at a screen of the device, but
according to the second protocol, a second type of indication different from the first type is displayed at the screen.

11. The medical device of claim 1, in which
the medical device exhibits a warning about the authentication not being confirmed when operating according to the second protocol, but not when operating according to the first protocol.

12. The medical device of claim 1, in which
according to the first protocol, the device has the capability of operating in both a manual mode and an AED mode, but
according to the second protocol, the device has the capability of operating in the AED mode but not in the manual mode.

13. The medical device of claim 1, in which
while a functionality of defibrillating is operable according to both the first protocol and to the second protocol,
a certain functionality other than the functionality of defibrillating is operable according to the first protocol, but not according to the second protocol.

14. The medical device of claim 13, in which
the certain functionality is an information display functionality.

15. The medical device of claim 13, in which
the certain functionality is a synchronized cardioversion therapy.

16. The medical device of claim 13, in which
the certain functionality is a pacing therapy.

17. The medical device of claim 13, in which
the certain functionality is to monitor a parameter of the patient.

18. The medical device of claim 17, in which
the parameter includes one of capnography, pulse oximetry, non-invasive blood pressure, end tidal CO2, ECG, invasive blood pressure, temperature, and CPR performance monitoring.

* * * * *

UNITED STATES PATENT AND TRADEMARK OFFICE
CERTIFICATE OF CORRECTION

PATENT NO. : 8,179,087 B2  
APPLICATION NO. : 12/760378  
DATED : May 15, 2012  
INVENTOR(S) : James S. Neumiller et al.

Page 1 of 1

It is certified that error appears in the above-identified patent and that said Letters Patent is hereby corrected as shown below:

On the title page item (56), Other Publications should read "International Preliminary Report on Patentability for PCT/US2009/045943, dated Sep. 1, 2010 (12 pp.)."
On page 2, Continuation of Other Publications should read "U.S. Appl. No. 12/760,331, James S. Neumiller, filed Apr. 14, 2010. International Search Report and Written Opinion of international application no. PCT/US2009/045943, mailed May 4, 2010, 14 pp. Response to Written Opinion for PCT/US2009/045943 filed Aug. 2, 2010. (18 pp.)."

Signed and Sealed this  
Twenty-fifth Day of September, 2012

David J. Kappos  
*Director of the United States Patent and Trademark Office*